United States Patent
Penanen et al.

(10) Patent No.: US 8,698,498 B2
(45) Date of Patent: Apr. 15, 2014

(54) LOW FIELD SQUID MRI DEVICES, COMPONENTS AND METHODS

(71) Applicant: California Institute of Technology, Pasadena, CA (US)

(72) Inventors: Konstantin I. Penanen, Glendale, CA (US); Byeong H. Eom, Pasadena, CA (US); Inseob Hahn, La Crescenta, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/916,514

(22) Filed: Jun. 12, 2013

(65) Prior Publication Data

US 2013/0271142 A1    Oct. 17, 2013

Related U.S. Application Data

(62) Division of application No. 13/090,931, filed on Apr. 20, 2011, now Pat. No. 8,487,623, which is a division of application No. 12/687,104, filed on Jan. 13, 2010, now Pat. No. 8,008,914, which is a division of application No. 12/113,130, filed on Apr. 30, 2008, now Pat. No. 7,671,587.

(60) Provisional application No. 61/008,127, filed on Dec. 18, 2007, provisional application No. 60/927,706, filed on May 4, 2007.

(51) Int. Cl.
*G01V 3/00* (2006.01)
*G01R 33/48* (2006.01)

(52) U.S. Cl.
USPC .............. 324/318; 324/300; 324/322

(58) Field of Classification Search
USPC ............. 324/300–322; 600/407–464
See application file for complete search history.

(56) References Cited

U.S. PATENT DOCUMENTS

| 7,053,610 | B2* | 5/2006 | Clarke et al. | 324/300 |
| 7,394,250 | B2* | 7/2008 | Itozaki et al. | 324/300 |
| 8,010,178 | B2* | 8/2011 | Seki et al. | 600/409 |
| 2004/0027125 | A1* | 2/2004 | Clarke et al. | 324/308 |
| 2007/0252595 | A1* | 11/2007 | Volegov et al. | 324/307 |

OTHER PUBLICATIONS

Non-Final Office Action mailed on Aug. 1, 2012 for U.S. Appl. No. 13/090,931, filed Apr. 20, 2011 in the name of Konstatin I. Penanen et al.
Notice of Allowance mailed on Apr. 2, 2013 for U.S. Appl. No. 13/090,931, filed Apr. 20, 2011 in the name of Konstatin I. Penanen et al.

* cited by examiner

*Primary Examiner* — Jermele M Hollington
*Assistant Examiner* — Emily Chan
(74) *Attorney, Agent, or Firm* — Steinfl & Bruno, LLP

(57) ABSTRACT

Low field SQUID MRI devices, components and methods are disclosed. They include a portable low field (SQUID)-based MRI instrument and a portable low field SQUID-based MRI system to be operated under a bed where a subject is adapted to be located. Also disclosed is a method of distributing wires on an image encoding coil system adapted to be used with an NMR or MRI device for analyzing a sample or subject and a second order superconducting gradiometer adapted to be used with a low field SQUID-based MRI device as a sensing component for an MRI signal related to a subject or sample.

3 Claims, 9 Drawing Sheets

LOW FIELD SQUID MRI DEVICES, COMPONENTS AND METHODS

CROSS REFERENCE TO RELATED APPLICATIONS

This application is a U.S. Divisional application of Ser. No. 13/090,931 filed on Apr. 20, 2011, which, in turn, is a U.S. Divisional application of Ser. No. 12/687,104 filed on Jan. 13, 2010 now U.S Pat. No. 8,008,914, which, in turn, is a U.S. Divisional application of Ser. No. 12/113,130, filed on Apr. 30, 2008 now U.S. Pat. No. 7,671,587, which, in turn, claims priority to U.S. Provisional Application 60/927,706 filed on May 4, 2007 and U.S. Provisional Application 61/008,127 filed on Dec. 18, 2007, the contents of all of which are incorporated herein by reference in their entirety. The present application may be related to U.S. patent application Ser. No. 12/113,163 for "Geometries For Superconducting Sensing Coils For SQUID-Based Systems" by Inseob Hahn, Konstantin I. Penanen and Byeong H. Eom, filed on Apr. 30, 2008, the contents of which are also incorporated by reference in their entirety.

STATEMENT OF GOVERNMENT GRANT

The invention described herein was made in the performance of work under a NASA contract, and is subject to the provisions of Public Law 96-517 (35 USC 202) in which the Contractor has elected to retain title.

FIELD

The present disclosure relates to magnetic resonance imaging (MRI). More in particular, it relates to SQUID MRI devices, components and methods.

BACKGROUND

Current conventional high-field magnetic resonance imaging (MRI) systems are not suitable for use in a typical doctor's office or in a mobile medical facility. A typical imaging system requires a large magnetic field (about 1 Tesla) that can be only achieved by operation of a large superconducting magnet at liquid helium temperature (about 4 K). Operation of the large field magnet at such temperature requires a special, dedicated facility such as a secured shielded room, a control room and an equipment room. This kind of arrangement is not easily affordable by a doctor. Therefore, it makes the system largely unavailable to disadvantaged populations. Other technical disadvantages are severe image distortions with in-vivo metallic implants and difficult intraoperability (e.g., imaging during surgery). Accidents associated with magnetic projectiles (a chair, an oxygen tank, etc) have also been reported.

Low field NMR using a superconducting quantum interference device (SQUID) detector, also known as SQUID NMR, has been recently used to study material properties. SQUID NMR techniques have also been applied to MRI imaging at low field, thus showing that superconducting magnets are not necessary for imaging. In addition, low field MRI showed an improved contrast imaging capability not achievable by conventional MRI. However, current low field SQUID MRI devices still require liquid helium cryogen service to operate the SQUID detector and the pick-up coil. Moreover, the imaging scanning time is too long. Also, the existing laboratory-based prototypes are designed with no transportability and intra-operability.

SUMMARY

According to a first aspect, a portable low field superconducting quantum interference device (SQUID)-based magnetic resonance imaging (MRI) instrument is provided, comprising: a sensing coil assembly to sense an MRI signal from a subject or sample; a SQUID to receive the MRI signal from the sensing coil assembly; a cryogenic cooler associated with the SQUID and the superconducting magnetic shield; an enclosure enclosing the sensing coil assembly, the SQUID, the superconducting magnetic shield and the cryogenic cooler; and a portable frame containing the enclosure and adapted to contain main field coils and field compensation coils.

According to a second aspect, a portable low field superconducting quantum interference device (SQUID)-based magnetic resonance imaging (MRI) system to be operated under a bed where a subject is adapted to be located is provided, comprising: a sensing coil assembly to sense an MRI signal from the subject; a SQUID to receive the MRI signal from the sensing coil assembly; a superconducting magnetic shield between the sensing coil assembly and the SQUID; a cryogenic cooler associated with the SQUID and the superconducting magnetic shield; and an enclosure enclosing the sensing coil assembly, the SQUID, the superconducting magnetic shield and the cryogenic cooler, the enclosure adapted to be located under the bed.

According to a third aspect, a low field superconducting quantum interference device (SQUID)-based magnetic resonance imaging (MRI) device is provided, comprising: a sensing coil assembly to sense an MRI signal from a subject or sample; a SQUID connected to the sensing coil assembly by way of a superconducting flux transformer; a current-limiting component provided between the superconducting flux transformer and the SQUID; and readout circuitry associated with the SQUID, the readout circuitry comprising a SQUID array amplifier.

According to a fourth aspect, a low field superconducting quantum interference device (SQUID)-based magnetic resonance imaging (MRI) device is provided, comprising: a sensing coil assembly to sense an MRI signal from a subject or sample; a SQUID connected to the sensing coil assembly; and a polarization coil assembly, wherein geometry and location of the polarization coil assembly with respect to the sensing coil assembly is selected to limit current input to the SQUID by compensating a magnetic flux output by the sensing coil assembly.

According to a fifth aspect, a method of configuring a magnetic field adapted to be used with a nuclear magnetic resonance (NMR) or magnetic resonance imaging (MRI) device for analyzing a sample or subject is provided, the method comprising: providing a magnetic field configuration not requiring a static homogeneous magnetic field and having a magnitude monotonically varying on a direction, thus having a spin precession direction varying over the sample or subject.

According to a sixth aspect, a second order superconducting gradiometer adapted to be used with a low field superconducting quantum interference device (SQUID)-based magnetic resonance imaging (MRI) device as a sensing component for an MRI signal related to a subject or sample is provided, the second order superconducting gradiometer comprising: first and second end loops; and first and second middle loops located between the first and second end loops, wherein the first and the second middle loops are configured to be sensing loops and the first and second end loops are configured to be non-sensing loops of the second order superconducting gradiometer.

Further embodiments of the present disclosure are shown in the written specification, drawings and claims of this application.

DETAILED DESCRIPTION

Figure 1:
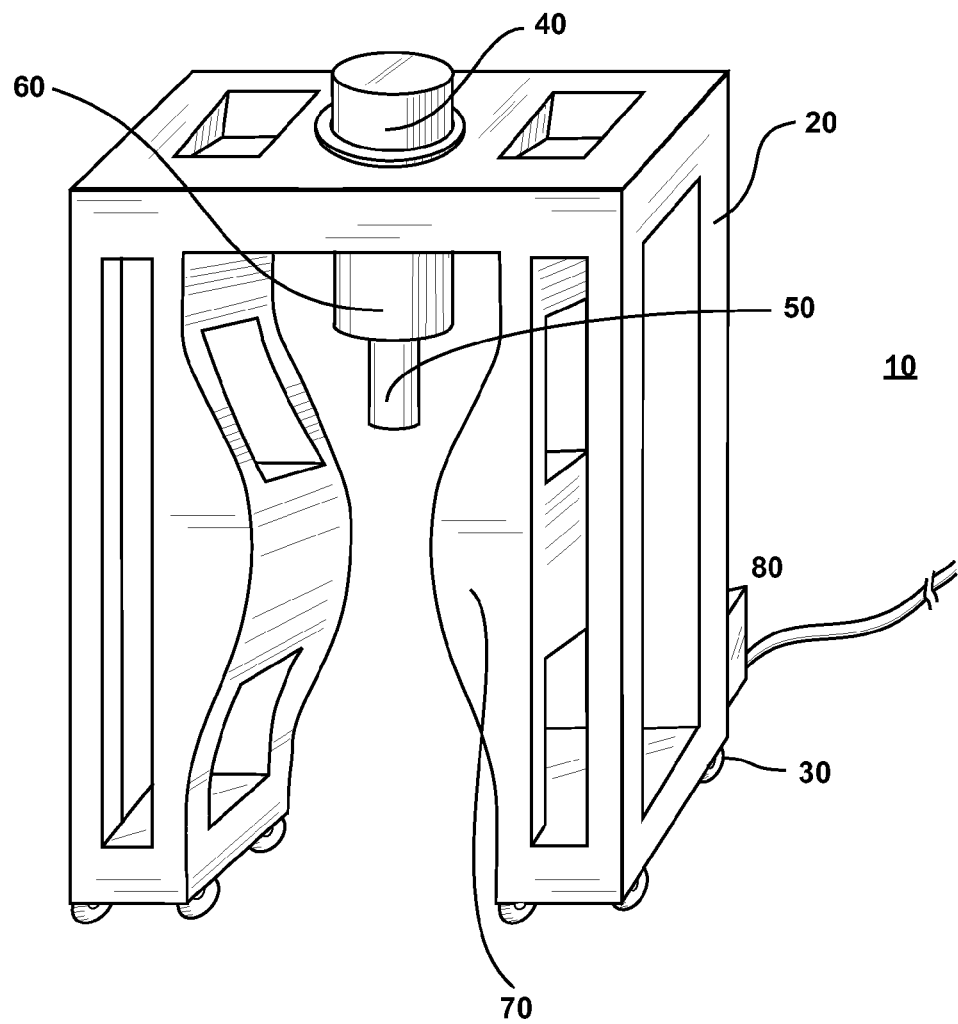
FIG. 1 shows a perspective view of a portable low field MRI instrument in accordance with the present disclosure.

FIG. 1 shows a perspective view of a portable low field SQUID MRI instrument (10) according to an embodiment of this disclosure. By way of example, the MRI instrument (10) shown in the figure can be about 2 m wide, have a height of about 2.5 m and a thickness of about 1.5 m.

A gradient field frame (20) is mounted on wheels (30) and is transportable. Gradient field frame (20) is a non-metallic, non-magnetic support structure containing field compensation coils, main field coils and field gradient coils. The magnetic fields due to currents in the coils are manipulated to produce various encoding sequences needed for MRI. The coils are operated by a computer.

The portable SQUID MRI instrument (10) also comprises a cryogenic cooler and shield assembly (40). In particular, a mechanical cryogenic cooler cools a sensing coil (50) and SQUID (superconducting quantum interference device) sensor (60) to their operating temperature. SQUIDs and cryogenic coolers (e.g., pulse tube cryogenic coolers) are known in the art as such and will not be described here in detail. The cryogenic cooler is contained within a vacuum enclosure. A shield (as later shown in FIG. 2) is used to isolate magnetic disturbance due to moving parts in the cryogenic cooler head. A cryogenic cooler compressor (not shown) can be either integrated with the frame (20), or located remotely of the portable instrument (10).

The sensing coil (50) is positioned in the bottom portion of the vacuum enclosure of the cryogenic cooler. Sensing coil (50) couples the magnetic signal from the subject to the SQUID sensor (60). The subject or sample to be imaged will be located under the sensing coil (50) in the space between the two vertical legs of the frame (20).

The SQUID sensor (60) is a highly efficient, low-noise current amplifier. Current due to a magnetic signal at the sensing coil (50) is detected by the SQUID (60). The resultant signal, combined with known encoding sequences, is used to reconstruct MRI images.

A polarization coil port (70) contains room-temperature or moderately cooled coils designed to pre-polarize nuclear spins of the subject in order to enhance the signal. The polarization field is switched off prior to the field encoding and signal acquisition sequences.

Also shown in FIG. 1 is a computer-controlled power source or power control unit (PCU) (80) for the field manipulation coils inside frame (20) and the polarization coils (70). The possible presence of wheels (30) makes the whole device very easy to transport.

Figure 2:
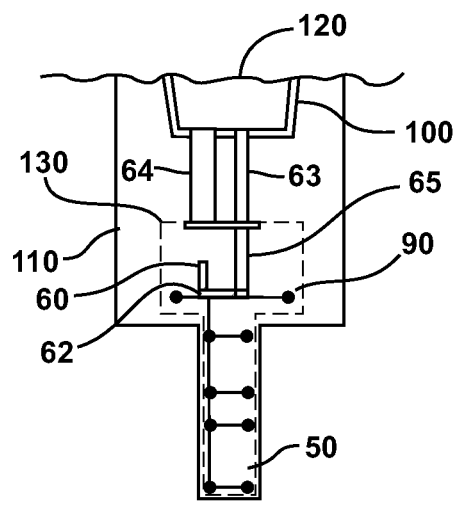
FIG. 2 shows a cross-sectional view of the portable MRI instrument of FIG. 1.

FIG. 2 shows a cross-sectional view of the portable MRI instrument of FIG. 1, where some of the components already introduced in FIG. 1 are better shown, such as sensing coil (50) and SQUID (60). Element (62) shows a heat exchanger under the SQUID (60). Also shown in the figure is a superconducting magnetic shielding (90), embodied by a superconducting plane mounted at the cold end of the cryogenic cooler (40). Superconducting plane (90) is designed to shield thermal magnetic noise from the metallic components of the cryogenic cooler and magnetic disturbance due to the moving parts of the cryogenic cooler.

According to one of the embodiments of the present disclosure, a high-permeability magnetic shielding (100) can be provided. Magnetic shielding (100) provides additional shielding from magnetic disturbances due to the moving parts of the cryogenic cooler (40). Also shown in FIG. 2 is a vacuum non-magnetic, non-metallic enclosure (110) of the cryogenic cooler. Further, a cryogenic cooler head (120) is also shown, together with cryogenic cooler pipes (63), (64), and (65). Cryogenic cooler head (120) contains root temperature cryogenic cooler components, and an optional compressor, as already explained with reference to FIG. 1. An example of cryogenic cooler suitable for use with the present embodiment is the Cryomech PT405/CP950 cryorefrigerator. A thermal shield (130) is tied to the intermediate stages of the cryogenic cooler and is designed to reduce radiative thermal load on the sensing or pick-up coil (50).

Figure 3:
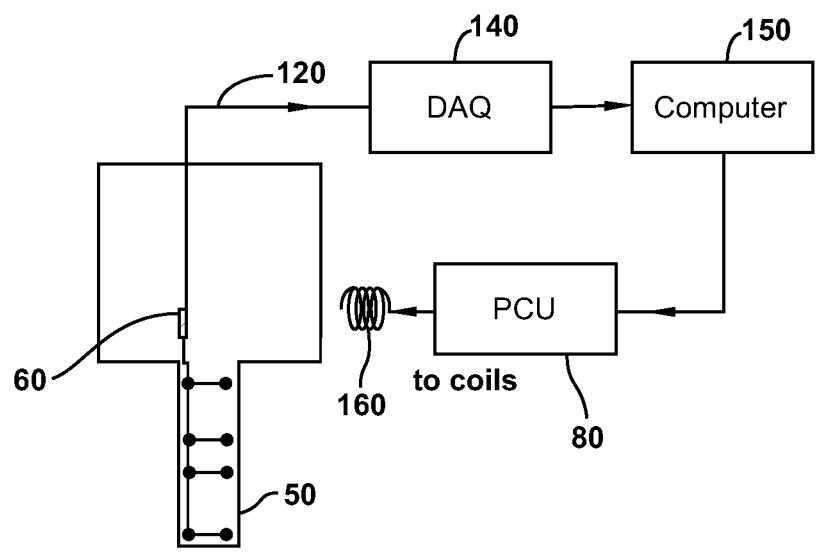
FIG. 3 is a schematic diagram showing connection between the SQUID and the all-field generating coils of the portable MRI instrument of FIGS. 1 and 2.

FIG. 3 is a schematic diagram showing connection between the SQUID and the all-field generating coils of the MRI instrument. In particular, a data acquisition amplifier (DAQ) (140) is connected to SQUID (60), a computer (150) is connected to DAQ (140), and the power control unit PCU (80) is connected to the computer (150). PCU (80) is connected to all-field generating coils (160) contained in frame (20).

It will be appreciated that the embodiments shown in FIGS. 1-3 eliminate need for helium cryogen that is required in existing laboratory units, because a SQUID sensor cooled by a cryogenic cooler is used. This makes the system virtually service-free and easy to operate using only electric power. By way of example, the mass of the entire system can be less than 150 lbs, including the data acquisition system shown in FIG. 3. As already discussed above, the size of the system can be less than 8 cubic meters with human body imaging in mind. The modular design-cryocooler enclosure, coil assemblies (polarizing, gradient, and others), electronics and frame-shown in FIGS. 1-3 makes it possible to assemble the system at any location. The person skilled in the art will also understand, upon reading of the present disclosure, that the system size can be easily customized depending upon the size of the sample.

Figure 4:
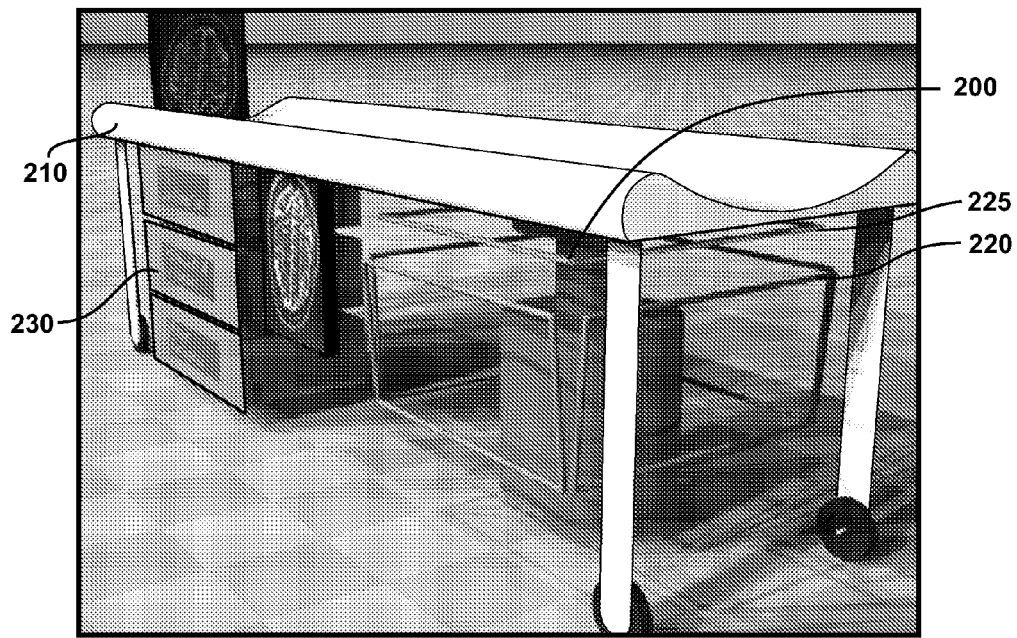
FIG. 4 shows an MRI bed system.

FIG. 4 shows an MRI bed system, according to a further embodiment of the present disclosure. An arrangement (200) is placed under a patient bed (210). The arrangement (200) comprises: 1) a cryogenic cooler with enclosure like the one shown in FIGS. 1 and 2; 2) a shielding like the one shown in FIG. 2; 3) a SQUID like the one shown in FIGS. 1 and 2 and 4) a sensing coil like the one shown in FIGS. 1 and 2. Also shown in FIG. 4 are field manipulation coils (220), shaped so as to produce field and gradients needed for encoding. For example, coil (225) represents the vertical field/gradient coil. The configuration shown in FIG. 4 allows all magnetic fields and gradients to be generated by a coil system localized entirely under the bed (220). The computer, PCU and DAQ are located as shown by reference numeral (230).

Figure 5:
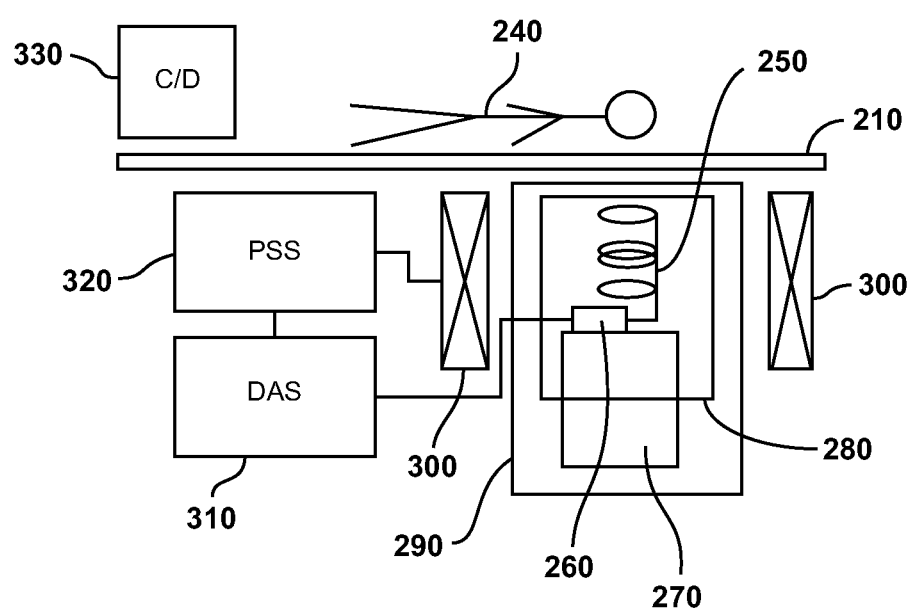
FIG. 5 shows a more detailed schematic view of the bed arrangement of FIG. 4.

FIG. 5 shows a more detailed schematic view of the bed arrangement of FIG. 4, showing a patient (240) on bed (210), a gradiometer sensing coil (250), a SQUID (260), a cryogenic cooler (270), an insulated container or dewar (280), an encloser (290), a polarization and encoding coil system (300), a controller and data acquisition system (310), a power supply system (320), and a console/display (330).

With reference to the embodiments of FIGS. 4 and 5, because only a very low static measurement field (less than about 1 mT) is necessary for low field SQUID MRI, the entire encoding field can be generated by a light weight one-sided coil system, i.e. cryogenic cooler interface and coils under the mobile bed as shown. This enables to construct a portable MRI bed system, with the coil system located under the patient bed. Use of a cryogenic cooler to cool down the sensing system makes the system shown in FIGS. 4 and 5 transportable to any location, without the need for liquid helium cryogens. The low field operation and open access enables surgery and diagnostic imaging on the same bed.

Figure 6:
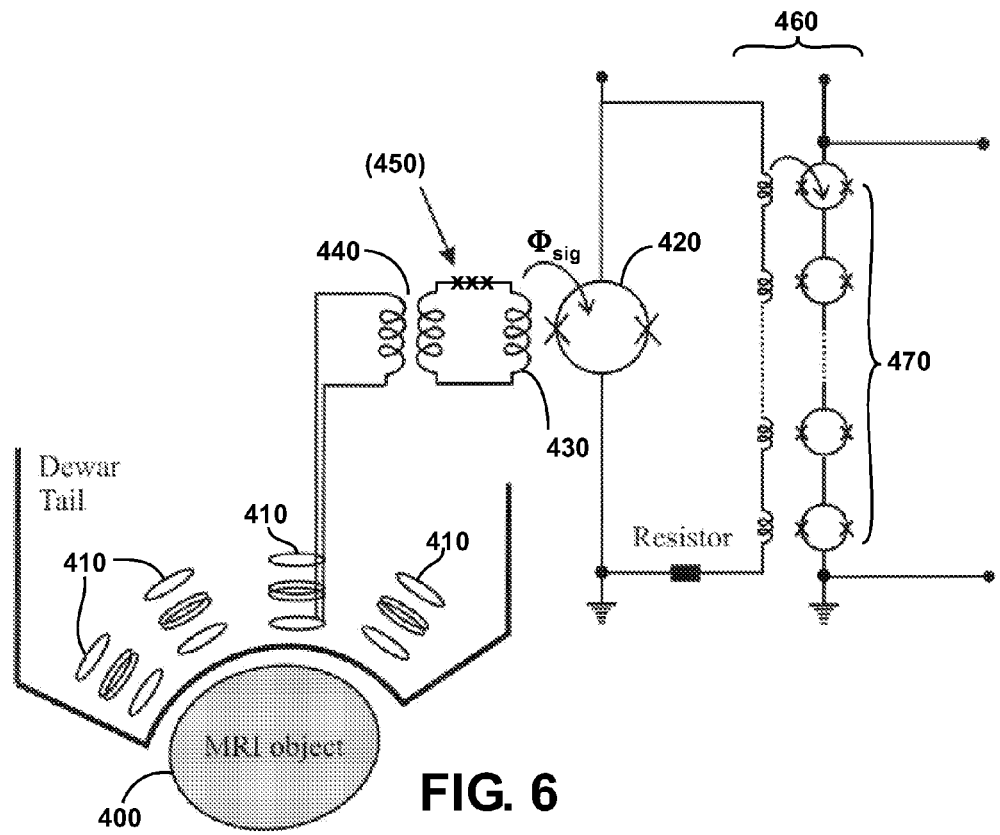
FIG. 6 shows an electric diagram of a further embodiment of the present disclosure, where a current limiting component is coupled with a SQUID array amplified readout.

FIG. 6 shows an electric diagram of a further embodiment of the present disclosure, where a current limiting component (450) is coupled with a SQUID array amplified readout (460). The MRI signal coming from an MRI object (400) is detected by superconducting second-order gradiometers (410) which are coupled to the SQUID (420) input coil (430) via a superconducting flux transformer (440). Generally speaking, a gradiometer is designed to be sensitive to the special variations of magnetic fields due to the presence of a sample or subject and remain insensitive to both uniform fields and linear (first order) gradients. During polarization of the object (400), the second order magnetic field gradient is much bigger than the MRI signal. If such gradient is directly fed into the SQUID (420), it may destroy the SQUID (420) or make it difficult to recover for measurement.

In order to overcome such problem, a current-limiting component (450) is provided between transformer (440) and SQUID input coil (430). Such "Q-spoiler" or "Q-killer" component acts as a resistor for high current values and as a superconductive path for currents having values less than a critical value, so as not to interfere with the MRI signal. In other words, when the critical current in a Josephson junction is exceeded, the junction effectively behaves as a resistor. By way of example, a Q-spoiler can be a number (e.g., about 200) of Josephson junctions connected in series.

Use of the current limiting component (450) is coupled with a readout circuit (460) comprising a SQUID array amplifier (470) inductively coupled to the SQUID (420). Such kind of arrangement is advantageous with respect to conventional pre-amplification and feedback readouts, because these readout systems add additional noise and constrain the bandwidth of the detectable signal. In addition, dedicated readout electronics for each SQUID is costly in a multi-channel SQUID system.

A further embodiment of the present disclosure relates to a compensation geometry compatible with coils of a SQUID low-field MRI device.

As noted in the previous embodiment, to mitigate the effects of induced currents, Q-spoilers can be employed. However, currents exceeding the critical current may introduce trapped flux in the Q-Spoiler Josephson junctions.

To overcome this problem, applicants have implemented a coil design that eliminates the need for Q-Spoiler circuitry and avoids overloading input superconducting circuitry. In a first realization of this embodiment, shown in FIG. 7, the polarization field is created by a combination of two polarization coils (410), (420) positioned symmetrically with respect to the sensing gradiometer (430), and connected in series. Final positioning adjustment is performed by introducing AC current into the polarization coils (410), (420) and nulling the resultant SQUID signal. Adjustment of 0.1 ppm is readily achievable. In other words, even with a complex field configuration it is possible to arrange the relative configuration of the coils in order to 1) cancel the influence of each source by symmetry and design and 2) allow for small adjustments to further cancel any residual influence due to imperfections of positioning and machining.

Figure 8:
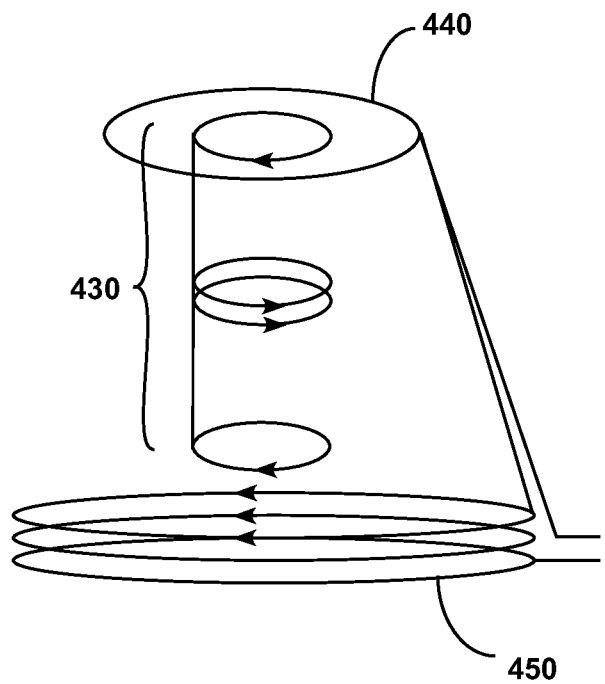
FIG. 8 shows a second example of a sensing coil and gradiometer compensation arrangement.

In certain configurations, symmetric design is not practical, and the polarization (or gradient, or excitation, to which the present teachings can also be applied) field is created by an asymmetric source with strong uncompensated field at the sense coil. In other words, the polarization coil generates a strong field at the position of the sensing coil. However, by symmetry it is possible to position the polarization coil in such manner that the net flux due to the polarization coil can be made zero. In this situation the field is strong and compensated. If the polarization coil were to be wound asymmetrically with respect to the sensing coil, the net flux through the sensing coil would be large and potentially damaging. It is, however, possible to add an additional coil, connected in series with the polarization coil, possibly smaller in size but positioned closer to one of the gradiometer loops, so that by design the net flux is cancelled. In other words, since the SQUID is sensing the output from a second-order gradiometer, it is possible to create compensation flux by placing a smaller coil (440), connected in series with the field-generating coil (450), in the close vicinity of the gradiometer (430) such that the net flux produced by the two cancel, as shown in FIG. 8. Compensation loops from several coils comprising the measurement system can be co-located. In other words, since the flux has to be canceled from many field manipulation coils (polarization, gradient, excitation etc), each field manipulation coil can have its own compensation loop or coil. Such compensation coils can be positioned in the same area in the vicinity of the sensing gradiometer, still allowing for fine adjustments.

Figure 7:
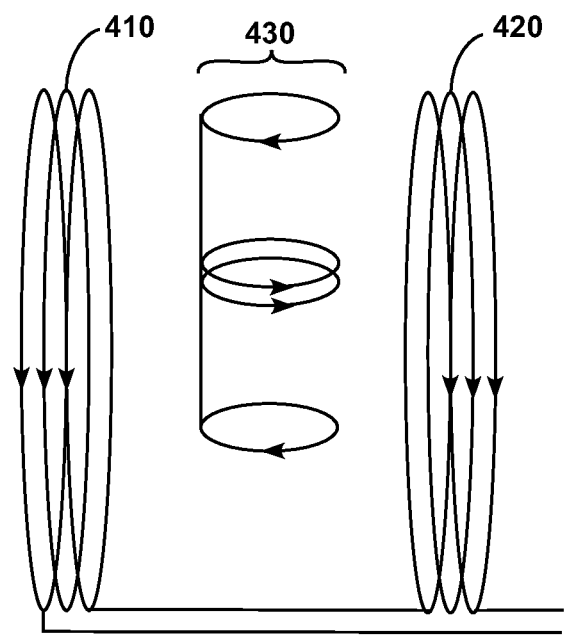
FIG. 7 shows a first example of a sensing coil and gradiometer compensation arrangement.

The embodiments of FIGS. 7 and 8 can also be applied to the embodiments of FIGS. 1 and 5.

A further problem in low field MRI is the long image acquisition time and/or the low image resolution due to small image encoding magnetic field gradients. Because of the fundamental properties of electromagnetism, image encoding gradients always entail undesirable concomitant fields. These fields are necessarily proportional to the encoding gradients, and result in image distortion or, in the case of phase encoding, image blurring. To reduce the distortion, the gradients should be small so that the total field variation is a small fraction of the static homogeneous field. However, the small gradients lengthen the image acquisition time and/or lower the image resolution because the image resolution is inversely proportional to the product of the gradient strength and the image acquisition time.

The present disclosure overcomes the above problems by providing a method of distributing an image encoding coil system. A magnetic field configuration (and the electric current configuration to produce such magnetic field configuration) is obtained, that is aimed at eliminating image distortion and blurring due to concomitant fields that accompany the encoding magnetic field gradient. This configuration reduces image acquisition time and/or improve image resolution in low static magnetic fields.

According to such embodiment, the restriction of uni-axial spin precession, and the linearity of field gradients typically present in conventional MRI are relaxed. In this way, a magnetic field configuration is obtained so that the magnitude of the field changes monotonically but nonlinearly along one direction. The field thus obtained can be used to encode a projection of the image. By rotating the field gradient for each projection, the image can be obtained using back projection reconstruction after linearizing each projection. The particular field configuration obtained in accordance with the teachings of the present disclosure can be applied in MRI and preferably in SQUID MRI.

(1) Relaxation of Restriction of Uni-axial Spin Precession by Providing for a Spin Precession Direction Varying Over the Sample In nuclear magnetic resonance (NMR), the sample is placed in a homogeneous (i.e. uniform in space) field. After applying a high-frequency pulse (spin excitation), the spins precess at the same rate throughout the sample, resulting in a narrow-band frequency response. In MRI, spatial encoding is achieved by varying the field across the sample or subject. This variation is typically achieved by adding a nominally uniform gradient to the static (i.e. non-changing) homogeneous field. Differently from prior art methods, in the method according to the present disclosure there is no static homogeneous field, as later specified in equations (1 to 3).

In nuclear magnetic resonance and MRI, the rotation frequencies of the spins are proportional to the local magnetic field strength and the precession directions are along the local magnetic field. In conventional MRI encoding, it is required that the spins precess along the same direction, i.e. along the large static field direction. A further difference between the present disclosure and the prior art is that the spin precession direction (i.e. the axis normal to the plane of precession created by the precession of the spin) varies over the sample. In particular, the position of the spin can be encoded by the rotation frequency whatever the precession direction is, as shown below.

(2) Obtain a Magnetic Field Configuration Whose Magnitude Changes Monotonically Over One Direction To obtain a field configuration whose magnitude changes monotonically along one direction, the Maxwell equations can be solved in 2-dimension (x-y plane) for static magnetic field with a constraint, as in equations 1 to 3.

$$\nabla \cdot B = 0 \qquad (1)$$

$$\nabla \times B = 0 \qquad (2)$$

$$|B| = F(x), \text{ where } F(x) \text{ is a monotonic function of } x \qquad (3)$$

The solution can be written with practical generality as, $$B = B_0 e^{x/a} \left[ \hat{x} \cos\left(\frac{y - y_0}{a}\right) - \hat{y} \sin\left(\frac{y - y_0}{a}\right) \right], \qquad (4)$$

where $B_0$, $a$, $y_0$ are arbitrary constants of proper dimensions.

As $|B| = B_0 e^{x/a}$, this field encodes a projection with the position x as a function of frequency f as, $$x = a \ln\left(\frac{2\pi}{\gamma B_0} f\right), \qquad (5)$$

where $\gamma$ is the proton magnetic moment divided by $\hbar$

If $x/a < \sim 1$, the projection can be linearized with tolerable resolution change over the entire projection.

(3) Obtain an Electric Current Configuration to Produce the Above Magnetic Field Configuration in the Case of a Cylindrical Surface For practical simplification, $y_0$ is set to 0. Then the electric current configuration on a long (length 2d>>radius b) cylindrical surface with its axis along z direction (FIG. 9) to produce the desired field inside the cylinder is, $$K = \hat{z} \frac{2B_0}{\mu_0} \sin\left(\frac{b}{a}\sin\theta + \theta\right) \exp\left(\frac{b}{a}\cos\theta\right), \text{ where } \theta = \tan^{-1}\frac{y}{x} \qquad (6)$$

Figure 9:
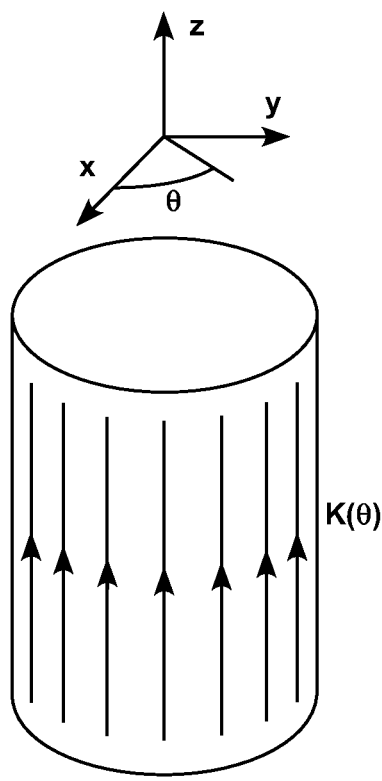
FIG. 9 is a perspective view showing current distribution on wires on an image encoding coil system.

The current distribution can be implemented using discrete wires with uniform distribution of spacing between them varying the current in each wire using dedicated current supplies, or with a proper distribution of spacing between the wires carrying the same current, as shown in FIG. 9. The angle θ represents the angular spacing between the wires.

(4) Magnetic Field Configuration and Electric Current Configuration Applied to SQUID MRI (to Rotate the Current Configuration Electrically, the Configuration is Expanded as Trigonometric Harmonics; by Changing Relative Amplitudes of the Sine and the Cosine Terms in Each Pair of Harmonics, the Current Configuration can be Rotated)

In SQUID MRI, the spins are pre-polarized in a high magnetic field. If the polarizing field is along the z direction and after polarizing the spins the polarizing field is turned off non-adiabatically fast so that the magnetization remains closely along z direction, the spins will start to precess along the local encoding field whose direction is normal to the z direction. The sensing loop for SQUID is placed to detect the z component of magnetization.

To obtain a family of back-projections necessary to reconstruct the 2-D distribution of spin densities, the field configuration or the sample need to be rotated. There can be many implementations to rotate the field configuration, including mechanical rotation of coils. To rotate it electrically, the field and the current are expanded as harmonics of θ when b<a.

$$B = B_0 \sum_{n=0}^{\infty} \frac{1}{n!} \left(\frac{r}{a}\right)^n (\hat{x} \cos n\theta - \hat{y} \sin n\theta) \qquad (7)$$

$$K = \hat{z} \frac{2B_0}{\mu_0} \sum_{n=0}^{\infty} \frac{1}{n!} \left(\frac{b}{a}\right)^n \sin(n+1)\theta \qquad (8)$$

For a projection of angle α, θ → θ + α so that

-continued $$K_\alpha = \hat{z}\frac{2B_0}{\mu_0}\sum_{n=0}^{\infty}\frac{1}{n!}\left(\frac{b}{a}\right)^n[\cos(n+1)\alpha\,\sin(n+1)\theta+\sin(n+1)\alpha\,\cos(n+1)\theta] \quad (9)$$

Therefore, a projection at any angle can be produced from the pairs of $\sin(n+1)\theta$ and $\cos(n+1)\theta$ current distributions by varying their relative magnitudes as $\cos(n+1)\alpha$ and $\sin(n+1)\alpha$, respectively.

For practical implementation, b/a can be restricted to ~0.1. Then the resolution change inside the cylinder is only ~20%, which can be easily linearized. Also, the series expansions for B and K converge rapidly, so that only a small number (about 5) of coil pairs are necessary for a typical MRI resolution.

For 3-dimensional or slice-selective encoding, there can be many compatible encoding schemes. Because the polarizing field is strong (~0.1 T), a small linear gradient ($B=\hat{z}G_z z$) can be added with negligible concomitant field effect. While polarizing, magnetization removing pulses, for example, repetitive 90° pulses, can be applied with a proper frequency profile to prevent polarizing other than in the selected slice.

Figure 10:
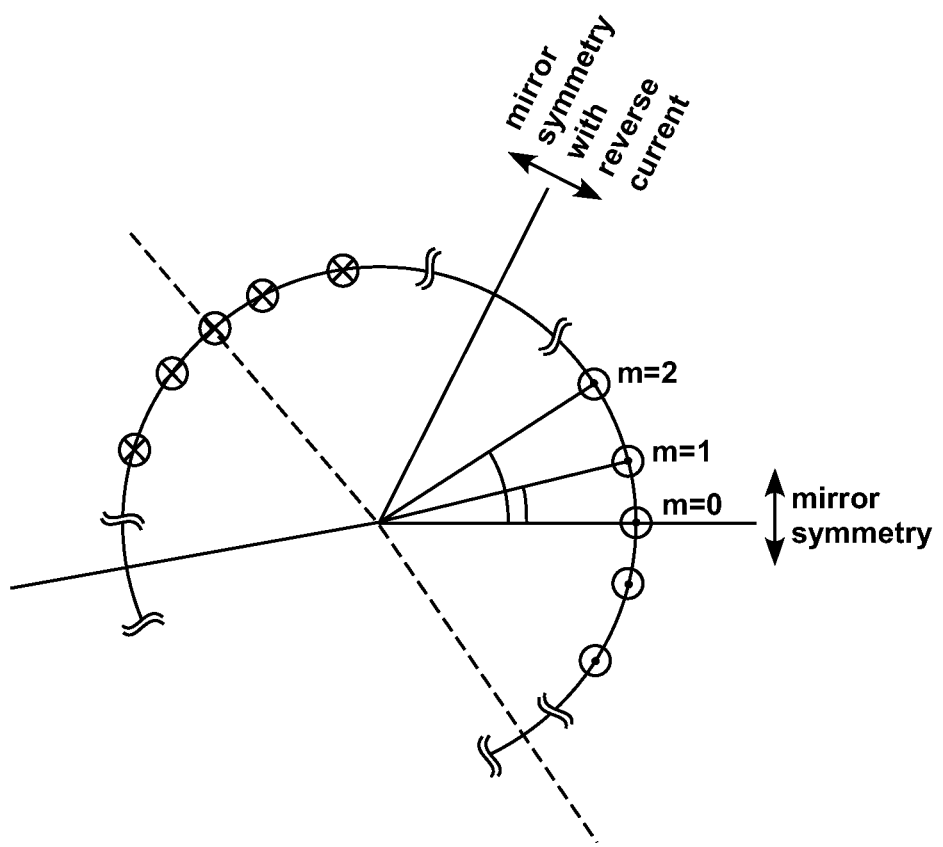
FIG. 10 is a cross-sectional view showing distancing between wires on an image encoding coil system.

FIG. 10 shows a cross-sectional view of an implementation of the cylindrical wire distribution for the $\cos(n+1)\theta$ term. For $$\frac{1}{4(n+1)}$$

portion and one shared wire, the angular position of the wires is given as $$\theta_m = \frac{1}{n+1}\sin^{-1}\frac{m}{M+1},$$

where m=0 to M and the total number of wires is 2(n+1)(2M+1).

For the term $\sin(n+1)\theta$, the wire distribution is rotated by $$\frac{\pi}{2(n+1)}.$$

In particular, FIG. 10 shows an example of the wire distribution on the cylindrical surface, which has a wire number density (proportional to current density) of $\cos(n+1)\theta$. The $\theta_m$ expression shown above is for a quarter of a period of the sinusoidal function. Such expression has to be duplicated mirror-symmetrically to make a half period, and then the half period has to be duplicated with reversed current to make a period. For the whole wire distribution for $\cos(n+1)\theta$, the period has to be repeated (n+1) times.

The present disclosure will now deal with an improved method for placing a second order gradiometer with respect to a patient in a SQUID MRI device. In particular, according to this embodiment, the second order gradiometer uses middle loops as sensing elements. This new scheme increases the sensitivity of the second order gradiometer and makes it more uniform, compared to the conventional side loop sensing scheme with a comparable matching SQUID.

In particular, in low field SQUID MRI, superconducting gradiometers are commonly employed as sensing elements to reject interference from distant sources. Second order gradiometers like the one shown in FIG. 11 achieve sufficient rejection so that the systems can be run in a minimally shielded environment. For effective coupling of the flux from the imaged object (placed under the cryostat bottom at room temperature), the cryostat wall (510) adjacent to the loops (520) in one side is constructed as thin as possible and these loops (520) are primarily used for sensing NMR signals from the sample.

For optimal coupling to SQUID, the inductance of the gradiometer should be matched to that of the SQUID input coil. In order to do so, the inductance of the sensing coil should be made as close as practicable to that of the SQUID input coil. For example, for a given geometry, the inductance can be increased by adding additional co-located loops to the gradiometer of FIG. 11, where it is shown that the gradiometer has two such co-located loops for each of the four positions.

Figure 11:
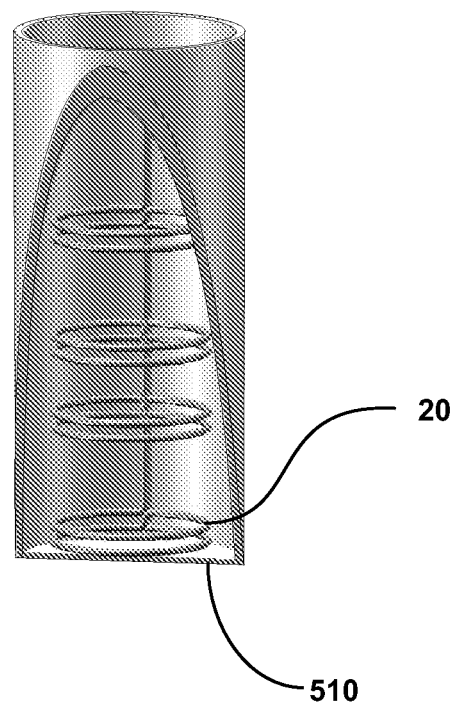
FIG. 11 shows a prior art configuration of a second order gradiometer.

In a typical configuration of SQUID MRI shown in FIG. 11, the sensitivity of a gradiometer is a rapidly decreasing function of the distance from the sensing loops. This results in severe non-uniformity of sensitivity and signal to noise ratio (SNR) in the image. This problem may be solved by using two second order gradiometers positioned at the opposite sides of the imaging volume, with two SQUIDs, one per gradiometer. However, it is not cost effective because SNR improves only by √2 at the center of the imaging volume. If the two gradiometers are connected to a single SQUID, the required inductance matching is more difficult to achieve due to larger inductance of the combined coil system. There is also the geometric problem of housing lengthy gradiometers when the volume for the gradiometers is limited.

Figure 12:
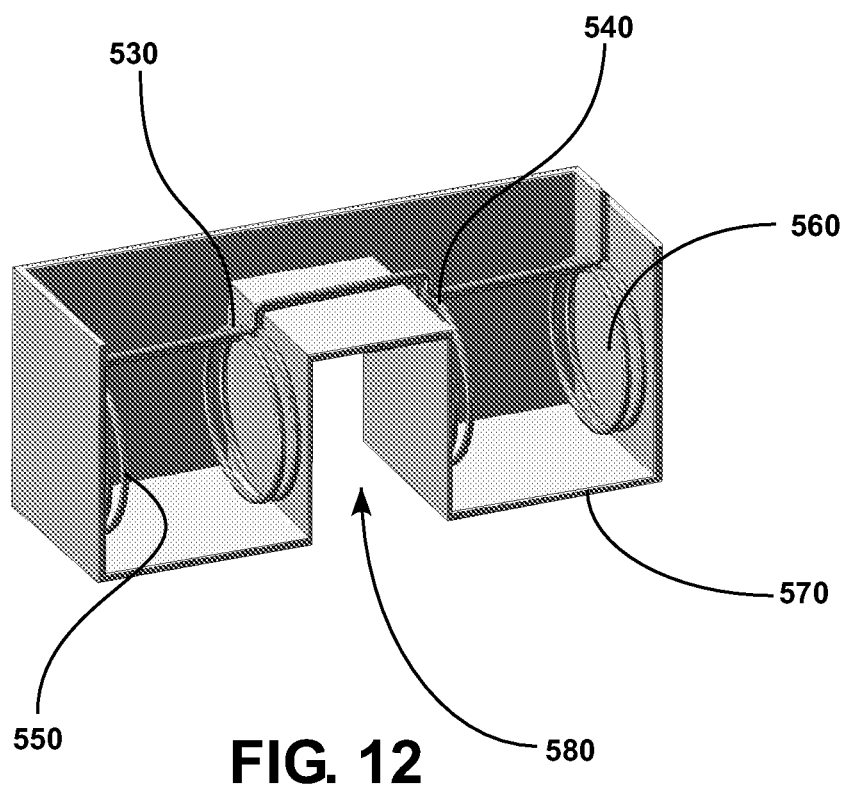
FIG. 12 shows a representation of a second order gradiometer in accordance with the present disclosure.

On the other hand, the new design in accordance with the present disclosure uses a single second order gradiometer where two middle loops (530), (540) are used for sensing, as shown in FIG. 12. Both the SNR and the uniformity of the gradiometer are greatly improved. In this scheme, the space between the two middle loops becomes the imaging volume with the enclosing cryostat built accordingly.

Figure 13:
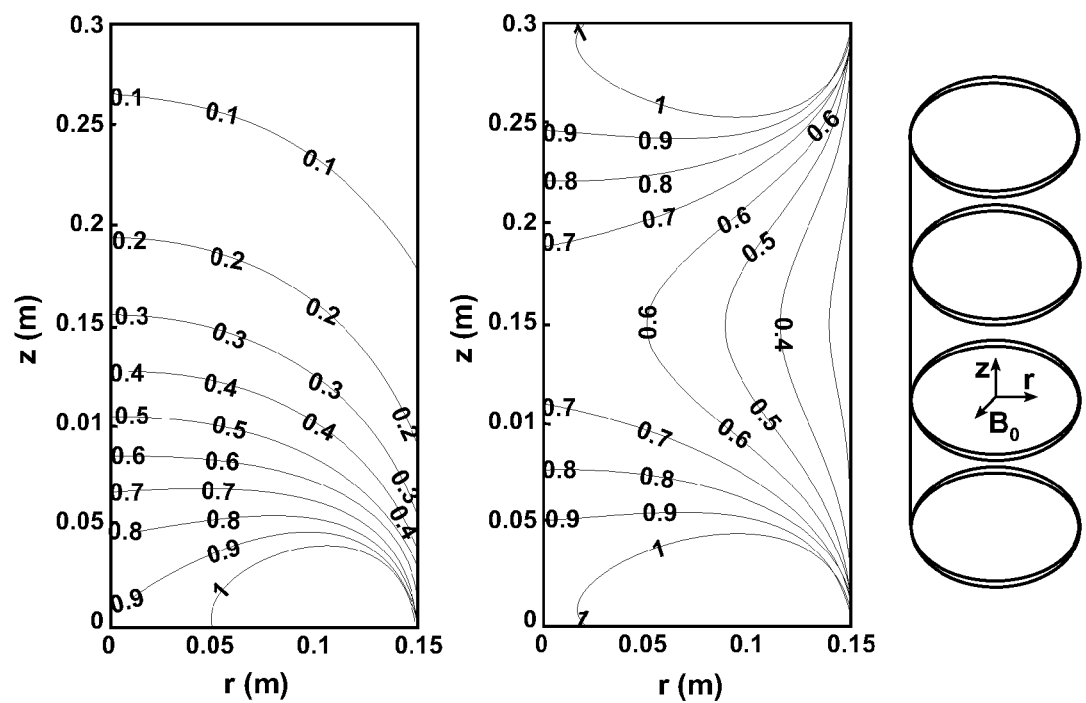
FIG. 13 shows a comparison between sensitivity profiles of a second order prior art gradiometer and a second order gradiometer according to the present disclosure.

Because of the two loops (530), (540) at each side of the imaging volume, the sensitivity at the center of the imaging volume is twice that of the conventional geometry (side loop sensing). Only about half of the induced energy is not utilized in the non-sensing loops (550), (560). The symmetric placement of the sensing loops (530), (540) provides a more uniform sensitivity. There is no inductance matching penalty associated with the new configuration because the geometry and the inductance remain to be that of a single second order gradiometer, as also shown in FIG. 13, where comparison between sensitivity profile of a second order prior art gradiometer (left side) and a second order gradiometer according to the present disclosure (right side) is shown.

Accordingly, what has been shown are low field SQUID MRI devices, components and methods. While these low field SQUID MRI devices, components and methods have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

The invention claimed is:

1. A method of configuring a magnetic field used with a nuclear magnetic resonance (NMR) or magnetic resonance imaging (MRI) device for analyzing a sample or subject, the method comprising:

providing a magnetic field configuration not requiring a static homogeneous magnetic field and having a magnitude monotonically varying on a direction, thus having a spin precession direction varying over the sample or subject; and providing an electric current configuration that comprises determining spacing between wires based on an angular distance between the wires on a cylindrical carrier body.

2. The method of claim 1, wherein the method is applied to a low field SQUID-based MRI device.

3. The method of claim 1, wherein the electric current configuration is expanded as trigonometric harmonics.

* * * * *